United States Patent
Andersen et al.

(10) Patent No.: US 9,228,937 B2
(45) Date of Patent: Jan. 5, 2016

(54) OPTICAL SPECTROMETERS

(75) Inventors: Mads Andersen, Copenhagen (DK); Thomas Nikolajsen, Slangerup (DK); Mogens Velsing, Birkeroed (DK); Bjarne Mølsted, Stenloese (DK)

(73) Assignee: FOSS ANALYTICAL A/S, Hilleroed (DK)

( * ) Notice: Subject to any disclaimer, the term of this patent is extended or adjusted under 35 U.S.C. 154(b) by 0 days.

(21) Appl. No.: 14/395,756

(22) PCT Filed: May 25, 2012

(86) PCT No.: PCT/EP2012/059883
§ 371 (c)(1),
(2), (4) Date: Oct. 20, 2014

(87) PCT Pub. No.: WO2013/174448
PCT Pub. Date: Nov. 28, 2013

(65) Prior Publication Data
US 2015/0090880 A1    Apr. 2, 2015

(51) Int. Cl.
*G01J 5/02* (2006.01)
*G01N 21/35* (2014.01)
*G01N 21/3577* (2014.01)
*G01J 3/02* (2006.01)
*G01N 21/03* (2006.01)
*G01N 21/85* (2006.01)

(52) U.S. Cl.
CPC ............... *G01N 21/35* (2013.01); *G01J 3/027* (2013.01); *G01J 3/0291* (2013.01); *G01N 21/0303* (2013.01); *G01N 21/3577* (2013.01); *G01N 21/8507* (2013.01); *G01N 2021/036* (2013.01); *G01N 2021/0375* (2013.01); *G01N 2021/0396* (2013.01); *G01N 2201/0668* (2013.01)

(58) Field of Classification Search
CPC ............ G01N 21/0003; G01N 21/253; G01N 21/7746; G01N 2015/1451
See application file for complete search history.

(56) References Cited

U.S. PATENT DOCUMENTS

2006/0074509 A1* 4/2006 Di Fabrizio et al. .......... 700/117
2006/0182659 A1  8/2006 Unlu et al.
2010/0182599 A1  7/2010 Albin et al.

FOREIGN PATENT DOCUMENTS

| JP | 2003307408 A | 10/2003 |
|----|--------------|---------|
| JP | 2006023088 A | 1/2006 |
| WO | WO-9705472 A1 | 2/1997 |
| WO | WO-2011069549 A1 | 6/2011 |

OTHER PUBLICATIONS

International Search Report PCT/ISA/210 for International Application No. PCT/EP2012/059883 Dated Jan. 30, 2013.

* cited by examiner

*Primary Examiner* — Kiho Kim
(74) *Attorney, Agent, or Firm* — Harness, Dickey & Pierce, PLC

(57) ABSTRACT

An optical spectrometer may include: an adjustable sampling space having two opposing side-walls between which in use a sample for analysis is charged and in at least one of which is formed an optical interface translucent to optical energy emitted by an optical energy source; an actuator mechanically coupled to one or both of the opposing side-walls and configured to operate in response to a command signal applied thereto to effect relative movement of the opposing side-walls; and/or an optical position sensor configured to detect interference fringes generated by the optical energy traversing a distance between the side-walls a plurality of times, having passed through the at least one optical interface, and configured to generate the command signal in dependence thereof. The adjustable sampling space may be brought into an analysis position at which the side-walls are relatively inclined to form a wedge shape.

14 Claims, 4 Drawing Sheets

OPTICAL SPECTROMETERS

The present invention relates to an optical spectrometer, in particular to one having an adjustable sampling space, and to a method of controlling such a spectrometer to adjust the adjustable sampling space.

Optical spectrometric analysis, in particular infra-red analysis, of sample material is well known and widely adopted in the measurement of the compositional properties of samples and for process monitoring and control. It is non-destructive, minimally invasive and many materials, particularly organic materials, show highly characteristic wavelength dependent absorption properties, particularly in the infra-red wavebands of the electromagnetic spectrum. Thus by measuring wavelength dependent absorption, particularly infra-red absorption, in a sample using typically transmission, reflection or transflectance analysis configurations, information concerning the physical structure and/or composition of a sample may be determined. Infra-red spectroscopy has been successfully utilised in the analysis of a wide variety of products including milk, cereal grains, oils, pharmaceuticals and bio-fuels. Whilst infra-red radiation is often employed it is well known that absorptions in other portions of the electromagnetic spectrum, from ultra-violet and the visible region, may also be utilised to characterise material compositional properties. Throughout the remainder of this document 'optical energy' will be used to describe energy from within the ultra-violet to the infra-red portion of the electromagnetic spectrum, with specific portions being referred to as the context demands, such as for example 'mid infra-red optical energy'

Increasingly, in industrial processes the measurement and monitoring of the contents of a process line or a reaction vessel is often required. It may be important to be able to follow a reaction inside a process tank or monitor the contents of a process line as it passes through the processing system without conducting their contents through a complicated by-pass system of pipelines with a pump, valves and a flushing arrangement. Such monitoring providing the possibility for real-time process control. Furthermore, in the pharmaceutical or food preparation industry it may be important minimise the interaction of the contents with external equipment which may increase the risk of contamination so that in-situ analysis is preferable.

It is known from WO 2011069549, of common applicant and the entire content of which is included herein by reference, to provide a spectrometer for performing spectrometric analysis in-line in a process environment. The spectrometer comprises a probe head having an adjustable sampling space which is intended for insertion in to material flowing in the process line. The sampling space is made up of two generally opposing, relatively movable, side-walls between which in use a sample for analysis is charged and in at least one of which is formed a widow translucent to optical energy emitted by an optical energy source. An actuator is coupled to one or both of the opposing side-walls and is operable in response to a command signal to effect their relative movement. A detector for generating a signal in dependence of the intensity of incident optical energy passing through the at least one window after its interaction with the sample is also provided as is a signal analyzer for analyzing a wavelength dependency of the so generated signal in order to determine characteristics of the sample therefrom. In use the actuator is operated to initially increase the distance between the two opposing side-walls which permits the sampling space to be charged with new material from the process line. The opposing side-walls are then moved to decrease the distance between them at which position the spectrometric analysis is made.

In order to provide reproducible analysis results from a spectrometer the separation of the two opposing side-walls, which in turn determines the amount of sample interacting with the optical energy, should be identical at each measurement, or at least known. A problem with known spectrometers is that the relative orientation of the two generally opposing side-walls is only measured indirectly through monitoring the movements of the actuator. Whilst this may provide accurate information regarding the relative movements of the side-walls the absolute orientation of the two side-walls is difficult to determine. Moreover the absolute orientation and separation of the side-walls will tend to change with mechanical changes to the spectrometer, such as mechanical wear or temperature and/or pressure induced mechanical changes.

It is an aim of the present invention to at least alleviate this problem. Accordingly the present invention provides a spectrometer comprising an adjustable sampling space having two generally opposing, relatively movable, side-walls between which in use a sample for analysis is charged and in at least one of which is formed a widow translucent to optical energy emitted by an optical energy source; and an actuator coupled to one or both of the opposing side-walls being operable in response to a command signal applied thereto to effect their relative movement. An optical position sensor is additionally provided as an element of the spectrometer which sensor is adapted to monitor the relative position of the side-walls by means of detecting the intensity of interference fringes (so-called Fabry-Perot interference fringes) which results from incident optical energy having passed through the at least one window after having traversed the distance between the side-walls a plurality of times. The command signal in generated in dependence of the detected interference fringes to cause the actuator to bring the two side-walls into a predetermined relative angular orientation at which interference fringe formation is mitigated.

Thus an absolute separation and/or angular orientation of the two opposing side-walls may be obtained through a direct optical measurement by the position sensor. This position may then be used in order to provide a know reference position from which the actuator may be operated to effect a relative movement of the side-walls to an analysis position for making a sample measurement. This analysis position is preferably a position at which the side walls are relatively inclined to form a wedge shape so that adjacent paths for the optical energy through the sampling space are different. The effects of optical interference are thereby mitigated. Movement to this analysis position may then be monitored through monitoring the movements of the actuator relative to the reference position. As an absolute determination is made then mechanical changes of both the actuator components and the window material itself may advantageously be compensated for in this manner.

Usefully, the optical position sensor is also adapted to generate wavelength dependent intensity signals used in the determination of characteristics, typically compositional characteristics, of a sample charged in the sampling space during a sample measurement.

In one embodiment measurement of the fringes may be made when the adjustable sample space is charged with a material of known refractive index, preferably material used in routine cleaning procedures between sample analysis measurements (water say). Knowledge of the refractive indices of the translucent material and of the material through which the optical radiation is transmitted permits a relatively simple calculation of wall separation in a well known manner.

These and other advantages of the present invention will become apparent from a consideration of the following description of exemplary embodiments which are made in connection with the drawings of the following figures of which:

Figure 1:
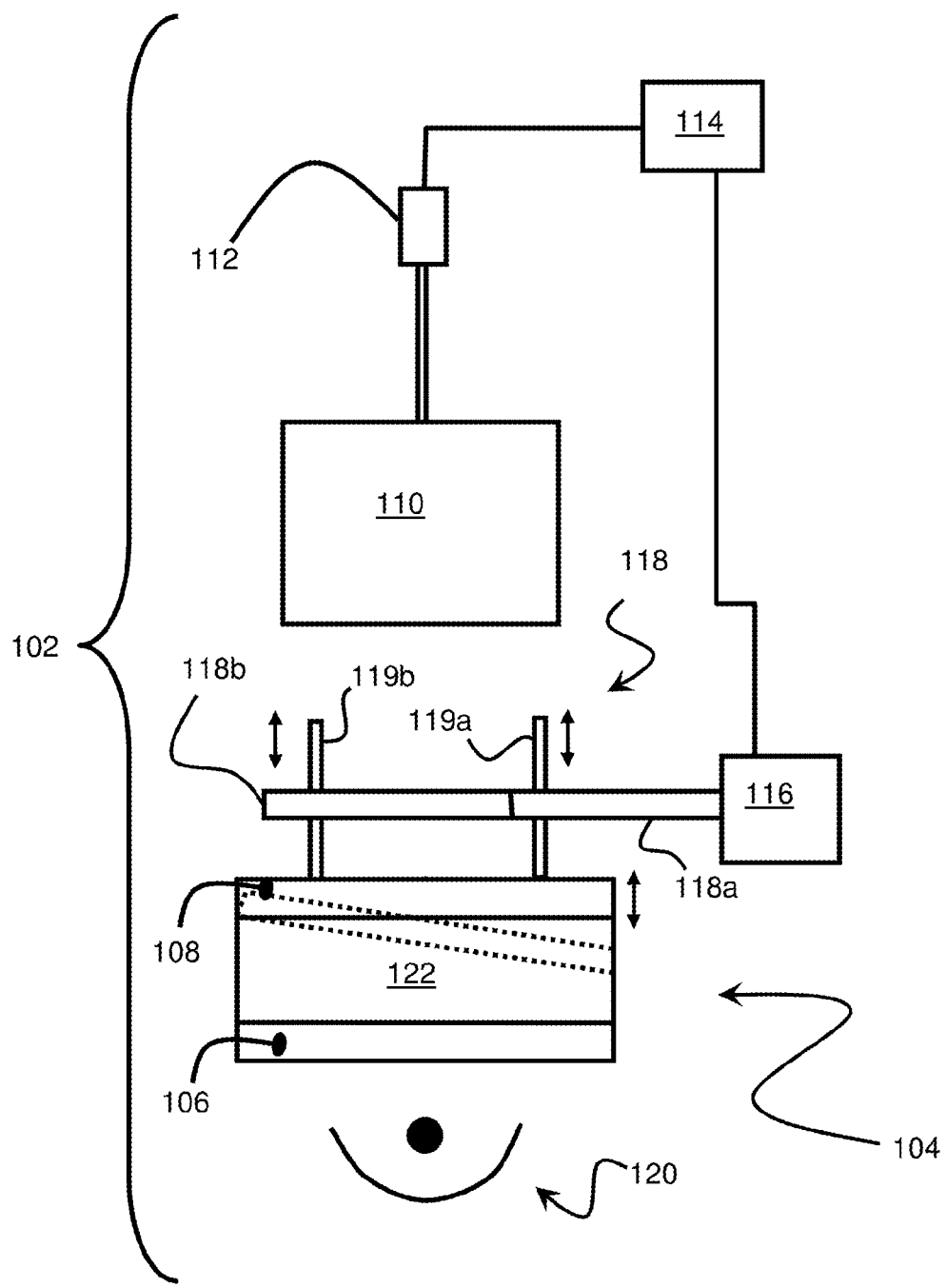
FIG. 1 illustrates generally an embodiment of a spectrometer according to the present invention.

Consider now an example of a spectrometer 102 according to the present invention that is illustrated in FIG. 1. The spectrometer 102 comprises an adjustable sampling space 104, which may for example be a component of a cuvette of a bench-top instrument or a component of a sample chamber of an on-line analyser. The adjustable sampling space 104 is here comprised of two generally planar, opposing and relatively movable side-wall sections 106,108, at least one of which (here both) being formed, at least in part with an optical interface made of material that is translucent in a radiation region of interest. The spectrometer 102 further comprises a spectral instrument 110 having a detector 112 optically coupled thereto; a signal processor 114 for processing a signal output by the detector 112 (the three components 110, 112 and 114 together forming an optical position sensor according to the present invention) and an actuator 116 which is connected via an adjustable mechanical coupling 118 to one or both (here one 108) relatively movable side wall sections 106, 108 to effect a movement of the same in order to generate a relative angular movement of one wall with respect to the other (illustrated by broken construction of wall 108) and also to generate relative translational movement (as illustrated by the double arrows), dependent on a command signal from the signal processor 114. In one example of the embodiment of the present invention which is illustrated in FIG. 1, the mechanical coupling may comprise a plurality (here two) individually controllable worm drive arrangements 118a, 118b. Each worm drive 118a, 118b has its associated worm 119a, 119b mechanically connected with the moveable wall section 108. Here the actuator 116 is configured to control movement of each worm 119a, 119b individually dependent on control signals from the signal processor 114 in order to effect the relative angular and/or translational movements.

The spectral instrument 110 may be of any known type, such as a monochromator or interferometer, which operates to generate an output Indexing intensity against an indication of a wavelength of optical energy input into the instrument 110. In the present embodiment the optical energy input into the instrument 110 is that energy emitted by an optical source 120 and having passed through a sample volume 122 internal of the adjustable sampling space 104 and delimited by the generally opposing side wall sections 106, 108. This is a so-called 'post dispersive' configuration of the spectrometer. In other, so-called 'pre-dispersive', configurations of a spectrometer according to the present invention the optical energy from the source 120 may be first input into the spectral instrument 110 and its output optically coupled into the sample volume 122.

The detector 112 is located to receive optical energy from the source 120 after its passage through the sample volume 122 and after being output from the spectral instrument 110. The detector 112 is configured to provide the output signal to the signal processor 114, having a characteristic value which is dependent on the intensity of the optical energy which it receives.

The signal processor 114 comprises computational means adapted through suitable programming to process the wavelength dependent signal from the detector 112 to identify any component thereof which originated from intensity variations at the detector which result from interference fringes (Fabry-Perot fringes) generated by the optical energy from the source 120 having traversed the distance between the side walls 106,108 a plurality of times before being incident on the detector 112. As discussed in greater detail below, the computational means of the signal processor 114 is further adapted to generate the command signal for the actuator 116 dependent on the identified Fabry-Perot interference fringes.

The same signal processor 114 may also be configured in a manner well known in the art to process the signal from the detector 112 in order to determine information concerning the physical structure and/or composition of a sample charged in the sample volume 122. In this manner the optical position sensor 110,112,114 of the spectrometer 102 according to the present invention may advantageously comprise those components employed to analyse samples.

Figure 2:
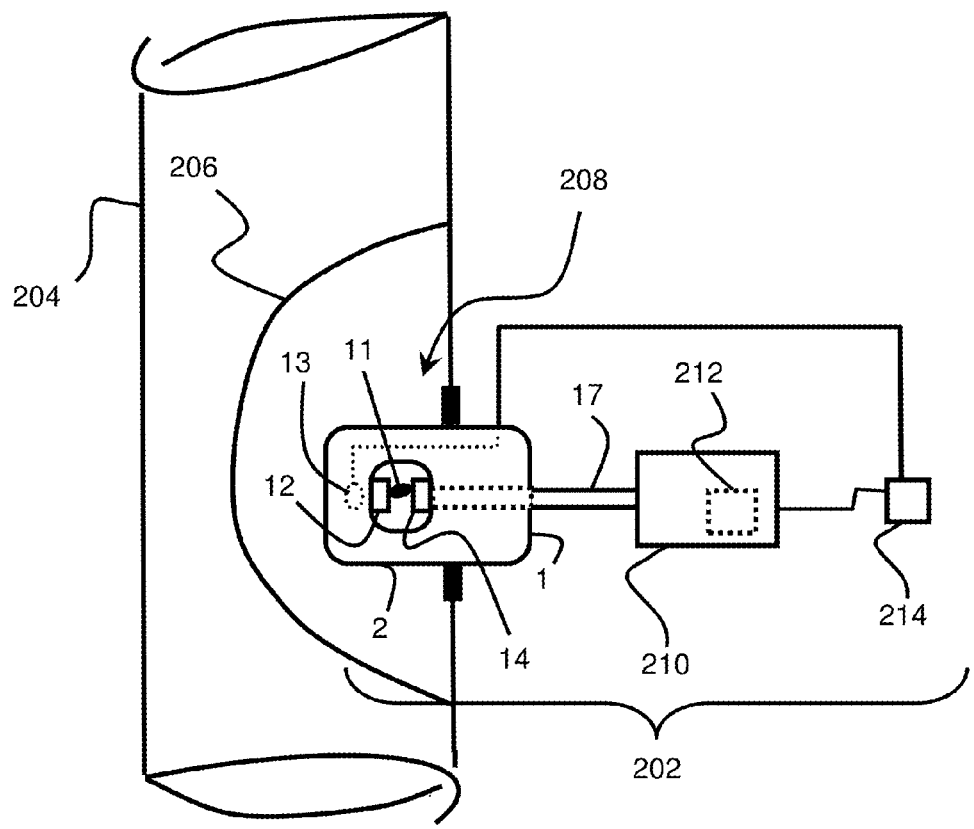
FIG. 2 illustrates an embodiment of a spectrometer according to the present embodiment configured for in-line monitoring.

Considering now a further embodiment of a spectrometer 202 according to the present invention which is illustrated in FIG. 2 as being located within a process pipe-line 204, as can be more easily seen from the cut-away portion 206 of that pipe-line 204. The spectrometer 202 comprises a probe 208 which will be described in greater detail below with reference to the drawings of FIGS. 3 and 4. Briefly, the probe 208 comprises an actuator portion 1 which is located primarily outside of the process-line 204 and a head portion 2 which is located primarily within the process-line 204. The head portion 2 is formed with a slotted sample space 11 through which, in use, a sample of material flowing in the pipe-line 204 may pass. Relatively moveable optical interfaces 12, 14 are located generally in opposition to one another within the sample space 11 to form an adjustable sampling space of the present invention. The spectrometer 202 additionally comprises a spectral instrument 210 optically coupled to internal the probe 208, here by means of a fiber optic 17; an optical detector 212 and a signal processor 214. These elements 210, 212 and 214 cooperating in a similar manner to that described in respect of the elements 110,112 and 114 of FIG. 1 to act as the optical position sensor according to the present invention.

Figure 3:
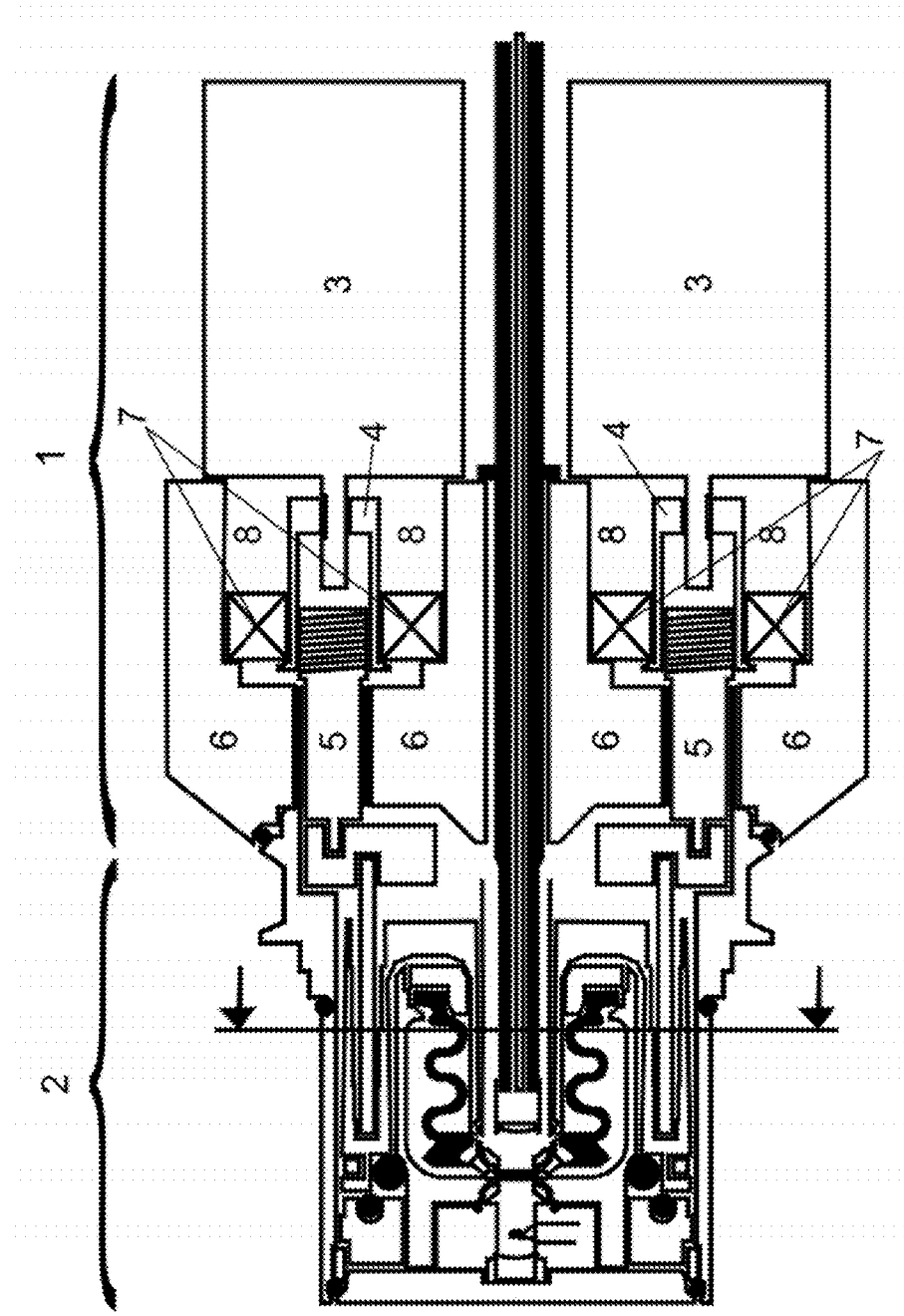
FIG. 3 illustrates a probe useable in the embodiment of FIG. 2.
Figure 4:
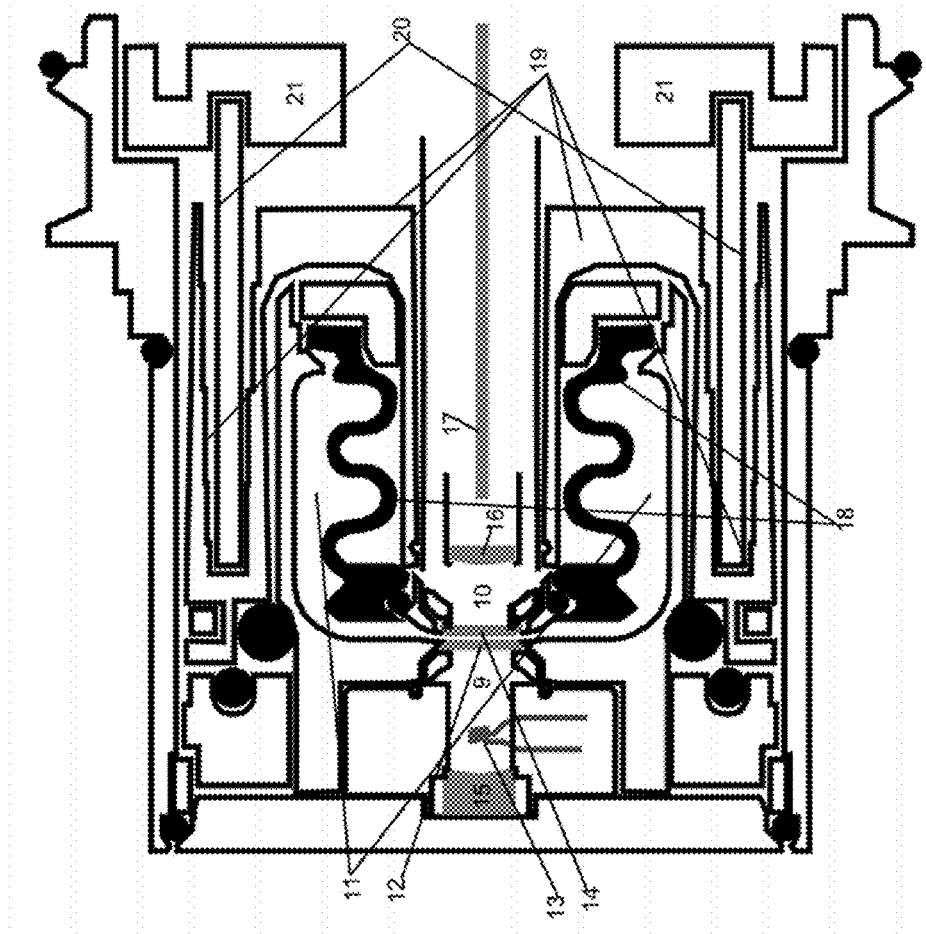
FIG. 4 illustrates the head portion of the probe of FIG. 3.

The probe 208, with reference to FIGS. 3 and 4, in the present embodiment may be considered to comprise two main portions; an actuator 1 and a head 2. The actuator 1 includes three independently controllable stepper motors 3 (two of which are illustrated in FIG. 3) that are each mechanically fixed to an associated finely threaded adapter 4. The adapter 4 is mounted in a ball-bearing 7 which is held against the associated motor 3 by biasing means (not shown) and a spacer 8 and connects to a push-rod 5. Thus, when the adapter 4 turns as the stepper motor 3 moves it drives the push rod 5 back or forth. The motors 3 are mounted on a block 6 that connects to the head 2 and are in the present embodiment placed in a 120 O geometry.

The head 2, with reference to FIG. 4, comprises a first inner cavity 9 and a second inner cavity 10 separated by the sample space 11. A planar optical interface 12 which is translucent to optical energy emitted by energy source 13 seals the first cavity 9 against ingress of material from the sample space 11. The optical energy source 13, here a source of mid infra-red radiation, is contained in the first cavity 9 and light from this is directed by a mirror 15 through the optical interface 12, the sample space 11 and a second planar optical interface 14 which is also translucent to the optical energy emitted by source 13. The light is collected by a lens 16 and launched into an optical fiber 17. The optical energy source 13 is provided with power from an external source (not shown) via electrical connectors which pass through a conduit in the probe head 2 and actuator 1. The second cavity 10 is sealed from the sample space 11 by the second optical interface 14 in cooperation with a flexible bellows diaphragm 18.

While the first optical interface 12 is fixed in the probe head 1, the position of the second optical interface 14 can be varied both with respect to distance from the first optical interface 12 and with respect to the orientation of the surface normal of the second optical interface 14 in relation to the surface normal of the first optical interface 12 (i.e. relatively angled). The movement is realised as the second optical interface 14 is mounted in a movement adapter unit 19. The movement adapter unit 19 is moved by three push rods 20 which are in turn each mechanically coupled via an associated connector plate 21 to an individual one of the push rods 5 of the actuator 1.

The bellow diaphragm 18 ensures the environmental sealing even when the optical interface 14 is moved.

It is important that in order to avoid Fabry-Perot type interferences in a sample spectrum the opposing side-walls are not parallel when the sample spectrum is being collected. According to WO 2011069549 this may be achieved by arranging for the actuator to move one or both of the walls in an arcuate motion about a hinge to thus ensure that the two opposing side-walls are never parallel.

The following is a description of an exemplary auto-alignment methodology which, when applied in the spectrometer according to the present invention, such as those spectrometers 102, 202 according to FIG. 1 or 2 respectively, ensures that measurements may be performed without having the walls either touch each other or produce Fabry-Perot type interferences in a sample spectrum. For ease of understanding the methodology will be described in relation to the spectrometer 202 which has been exemplified above with reference to the drawings of FIGS. 2 to 4.

In order to precisely determine the control parameters of the command signal which will cause the actuator 1 to align the two flat optical interfaces 12, 14 parallel to each other the following general procedure is employed:

The actuator 1 operates to control the motors 3 to move one interface (here the second interface 14) in relation to the other without changing the mean distance between the two. Practically that means that when one edge position of the moveable interface 14 is brought forward in order to enable a tilt, this is compensated with movement of the other edge positions to keep the mean distance between the two interfaces 12, 14 constant.

In this way it is possible, in a well-controlled manor, to vary the position of the moveable interface 14 in an angle space.

This is repeated a plurality of times, each time providing command signals causing the actuator 1 to operate in order to achieve a different relative angular orientation of the interfaces 12,14.

For each orientation a wavelength dependent intensity measurement is recorded using the optical position sensor, here comprising the cooperating spectral instrument 210 and detector 212 arrangement.

The signal processor 214 of the position sensor accesses the recorded measurements and compares them in order to calculate their difference, which primarily is the addition of Fabry-Perot fringes for the parallel realizations.

The most parallel position of the optical interfaces 12,14 at which their normal-vectors are substantially parallel, is then determined in the signal processor 214 by calculating therein the position of the motors 3 of the actuator 1 that will produce the largest fringe amplitude. This is used as a reference position.

The command signal is then constructed in the signal processor 214 having control parameters that when applied to the actuator 1 will cause a movement of the motors 3 to effect a relative tilting of the interfaces 12, 14 such that the angle between their normal-vectors is far enough away from this reference position to avoid (or at least minimise) the formation of the Fabry-Perot fringes.

Additionally, the distance between the two interfaces 12, 14 may be calculated from an analysis in the signal processor 214 of the fringe period, and the parameters of the command signal also constructed from this calculation to ensure that a desired mean distance is maintained.

With the interfaces 12, 14 so orientated to avoid (or at least minimise) fringe formation and preferably to also achieve a desired mean separation, sample spectra may be recorded for material charged between the two interfaces 12, 14 using the spectral instrument 210 and cooperating detector 212 of the position sensor. The same signal processor 214 may also be configured in a manner well known in the art to process the signal from the detector 210 in order to determine information concerning the physical structure and/or composition of the sample.

As a particular example of the application of the above method the use of the spectrometer 202 according to FIGS. 2-4 in the in-line monitoring of milk (refractive index of around 1.338) processing will be considered in which a Fourier transform interferometer, operating in the mid-IR spectral region, is utilized as the spectral instrument 210 and the optical interfaces 12, 14 are diamond windows (refractive index of around 2.147). The above is the description on the realization in fairly general terms. Experimentally it has been found that the fringes disappear when the angle between the normal-vectors of the two diamonds differ by 0.07 degrees. For diamond windows typically having a diameter of 8 mm and with a desire to have 10 µm mean spacing, the two diamond windows 12, 14 will touch at 0.21 degrees. This specifies the range of angles that the windows 12, 14 must be controlled within.

In the exemplary embodiment of the method according to the present invention the motors 3 steering the diamond window 14 are controlled in order to realize twenty eight relative positions of the windows 12, 14, and thus the data analysis is made on this set of twenty eight spectra. In the present embodiment the way the data is analysed is through known multivariate analysis techniques, preferably principal component analysis (PCA), in which the spectra are re-expressed as multiples of a series of common features. By removing the slowly oscillating common features all there is left are the Fabry-Perot fringes. It is then a matter of performing a Fourier transformation of the resulting Fabry-Perot fringes which yields the periodicity and amplitude of the fringes, which can be directly related to the distances between and to the parallelism of the two diamond windows 12, 14 respectively.

The continuous monitoring of the alignment of the optical interfaces (12, 14 for example) may be additionally or alternatively performed in the spectrometer (202 say) according to the present invention. According to this method of operation only two relative positions of the two interfaces 12,14 are used:
1. The first is a measurement of a spectrum where the one of the probe windows (14 say) is tilted by a fixed amount, which is characterized by being of a certain quantity ~0.07 deg, such that no fringes occur in the spectrum.

2. The second measurement is at the last-found parallel orientation while at the same mean distance as measurement made at step 1, described above. The parallel position being found using the auto-alignment procedure that was previously described.

Now it is possible to compare in the signal processor 214 the last N spectral measurements (step 1. above) with a single parallel measurement (step 2. above) in the same manner as in the auto-alignment procedure, and in this way extract the Fabry-Perot fringes. By measuring in this way a parallel measurement for every N spectral measurement it is possible to monitor if the amplitude or period of the Fabry-Perot fringes at the presumed parallel position starts to drift. If the amplitude falls to a predetermined level, say, half, of the initial amplitude obtained immediately, or very shortly after, an auto-alignment procedure, then a new auto-alignment procedure can be initiated and in this way ensure that the two optical interfaces 12, 14 remain at the same relative position (separation and/or angular orientation) and thus may compensate for mechanical changes in the spectrometer, such as thermo-mechanical changes, pressure dependent mechanical changes or wear of mechanical parts. Additionally or alternatively a sensible warning may be issued, typically when the degree of adjustment exceeds a predetermined threshold value indicating an excessive mechanical change so that servicing of the instrument may be performed.

By way of example only, the measurements of interference fringes using an instrument and a method according to the present invention may be performed in intervals between collection of sample spectra during which intervals the sample space is charged with a fluid of known refractive index, for example water (refractive index around 1.330). Usefully, this fluid may also be employed as a cleaning or flushing fluid.

The invention claimed is:

1. An optical spectrometer, comprising:
two generally opposing, relatively movable side-walls, defining an adjustable sampling space, between which in use a sample for analysis is charged and in at least one of which is formed an optical interface translucent to optical energy emitted by an optical energy source;
an actuator mechanically coupled to one or both of the opposing side-walls and configured to operate in response to a command signal applied thereto to effect relative movement of the opposing side-walls; and
an optical position sensor configured to detect interference fringes generated by the optical energy traversing a distance between the side-walls a plurality of times, having passed through the at least one optical interface, and configured to generate the command signal in dependence thereof;
wherein the position sensor is configured to process the detected interference fringes to determine therefrom a reference position of the actuator at which the two side-walls will be parallel, and configured to generate the command signal thereafter to effect movement of the actuator relative to the reference position so as to bring the side-walls into a predetermined relative angular orientation at which the interference fringe formation is mitigated, thus achieving a predetermined degree of non-parallelism of the side-walls and thereby bringing the adjustable sampling space into an analysis position at which the side-walls are relatively inclined to form a wedge shape, at which position sample analysis is performed.

2. The spectrometer as claimed in claim 1, wherein the position sensor is configured to measure an amplitude of the detected interference fringes as an indication of a degree of parallelism of the side-walls for use in determining the reference position.

3. The spectrometer as claimed in claim 1, wherein the position sensor is configured to measure a periodicity of the detected interference fringes as an indication of separation between the side-walls for use in determining the reference position.

4. The spectrometer as claimed in claim 1, wherein the position sensor is configured to generate a plurality of command signals, each one of which for causing a different predetermined relative movement of the side-walls, configured to record after each different relative movement resulting interference fringes, and, after the plurality of relative movements, to compare the recorded interference fringes to determine therefrom the reference position as a position at which an amplitude of components originating from the interference fringes will be maximised.

5. The spectrometer as claimed in claim 1, wherein the position sensor comprises a spectral instrument configured to generate an output indexing intensity of input optical energy against an indication of wavelength of the input optical energy.

6. A method of controlling adjustment of an adjustable sampling space in an optical spectrometer, the spectrometer comprising two generally opposing, relatively movable side-walls, defining the adjustable sampling space, between which in use a sample for analysis is charged and in at least one of which is formed an optical interface translucent to optical energy emitted by an optical energy source; an actuator mechanically coupled to one or both of the opposing side-walls and configured to operate in response to a command signal applied thereto to effect relative movement of the opposing side-walls; and an optical position sensor configured to detect interference fringes generated by the optical energy traversing a distance between the side-walls a plurality of times, having passed through the at least one optical interface, and configured to generate the command signal in dependence thereof; the method comprising:
detecting by the optical position sensor the interference fringes formed by the optical energy having traversed the adjustable sampling space between the opposing side-walls the plurality of times;
generating the command signal in dependence of the detected interference fringes to control operation of actuator so as to bring the two side-walls into a predetermined relative orientation for sample analysis at which interference fringe formation is mitigated by achieving a predetermined degree of non-parallelism of the side-walls; and
applying the command signal to the actuator to effect a dependent adjustment of the adjustable sampling space, thereby bringing the adjustable sampling space into an analysis position, at which the side-walls are relatively inclined to form a wedge shape.

7. The method as claimed in claim 6, wherein the generating of the command signal comprises:
analyzing the detected interference fringes to determine a reference position of the actuator at which the side-walls will be parallel; and
generating the command signal to effect movement of the actuator relative to the reference position so as to achieve the predetermined degree of non-parallelism of the side-walls.

8. The method as claimed in claim 7, further comprising:
generating a plurality of command signals, each of which for causing a different relative orientation of the side-walls;
recording, at each different relative orientation, the interference fringes detected by the optical position sensor; and
comparing electronically the recorded interference fringes to determine the reference position.

9. The method as claimed in claim 8, wherein the recording at each different relative orientation comprises:
recording an interferogram for each different relative orientation; and
processing the recorded interferogram, using a multivariate analysis within the optical position sensor, to remove spectral components not associated with the interference fringes; and
wherein the comparing electronically comprises subjecting each of the processed interferograms to Fourier transformation to yield a related signal a periodicity and amplitude of which is indicative of separation and parallelism, respectively, of the side-walls.

10. The method as claimed in claim 8, wherein the recording at each different relative orientation comprises:
recording an interferogram for each different relative orientation; and
processing the recorded interferogram, using a principal component analysis within the optical position sensor, to remove spectral components not associated with the interference fringes; and
wherein the comparing electronically comprises subjecting each of the processed interferograms to Fourier transformation to yield a related signal a periodicity and amplitude of which is indicative of separation and parallelism, respectively, of the side-walls.

11. The method as claimed in claim 6, further comprising:
charging the adjustable sampling space with a material of fixed refractive index before detecting the interference fringes.

12. The method as claimed in claim 11, wherein the material of fixed refractive index has a known refractive index, the value of which is used to determine the reference position.

13. The method as claimed in claim 11, wherein the material of fixed refractive index is water.

14. The method as claimed in claim 6, further comprising:
detecting a wavelength dependent intensity variation of the emitted optical energy after its interaction with a sample charged in the adjustable sampling space, when the side-walls are set at the predetermined relative orientation for sample analysis.

* * * * *